(12) United States Patent
Chibrac et al.

(10) Patent No.: US 6,540,786 B2
(45) Date of Patent: Apr. 1, 2003

(54) JOINT PROSTHESIS MEMBERS AND METHOD FOR MAKING SAME

(75) Inventors: Jean Chibrac, 7 Rue des Acacias, 33600 Pessac (FR); Jean-Pierre Gemon, 35 Rue Pierre Duhem, 33000 Bordeaux (FR); Alain Le Rebeller, Bordeaux (FR)

(73) Assignees: Jean Chibrac (FR); Jean-Pierre Gemon (FR)

( * ) Notice: Subject to any disclaimer, the term of this patent is extended or adjusted under 35 U.S.C. 154(b) by 0 days.

(21) Appl. No.: 09/754,044

(22) Filed: Dec. 27, 2000

(65) Prior Publication Data

US 2002/0022889 A1 Feb. 21, 2002

Related U.S. Application Data

(63) Continuation of application No. 09/029,121, filed as application No. PCT/FR96/01306 on Aug. 22, 1996, now abandoned.

(30) Foreign Application Priority Data

Aug. 23, 1995 (FR) .............................................. 95 10004

(51) Int. Cl.[7] .................................................. A61F 2/30
(52) U.S. Cl. .................................................. 623/18.11
(58) Field of Search .......................... 623/18.11, 20.14, 623/20.3, 20.31, 20.32

(56) References Cited

U.S. PATENT DOCUMENTS

| 3,964,106 A | * | 6/1976 | Hutter, Jr. et al. | ........ 623/18.11 |
| 4,355,429 A | * | 10/1982 | Mittelmeier et al. | ...... 623/18.11 |
| 5,059,209 A | * | 10/1991 | Jones | ........................... 623/23 |

* cited by examiner

*Primary Examiner*—Corrine McDermott
*Assistant Examiner*—A. Stewart
(74) *Attorney, Agent, or Firm*—Ostrolenk, Faber, Gerb & Soffen, LLP

(57) ABSTRACT

The invention relates to joint prosthesis elements, to a method of manufacturing prostheses, and to a kit for putting said prostheses into place. The prosthesis element which is put into place in a resection in the joint surface is defined by a contact surface C, a fixing surface F and, interconnecting said surfaces, a peripheral surface P which co-operates with a projecting rim R of the resection. An anchoring element A projects from the fixing face and penetrates into a corresponding anchoring hole D.

37 Claims, 9 Drawing Sheets

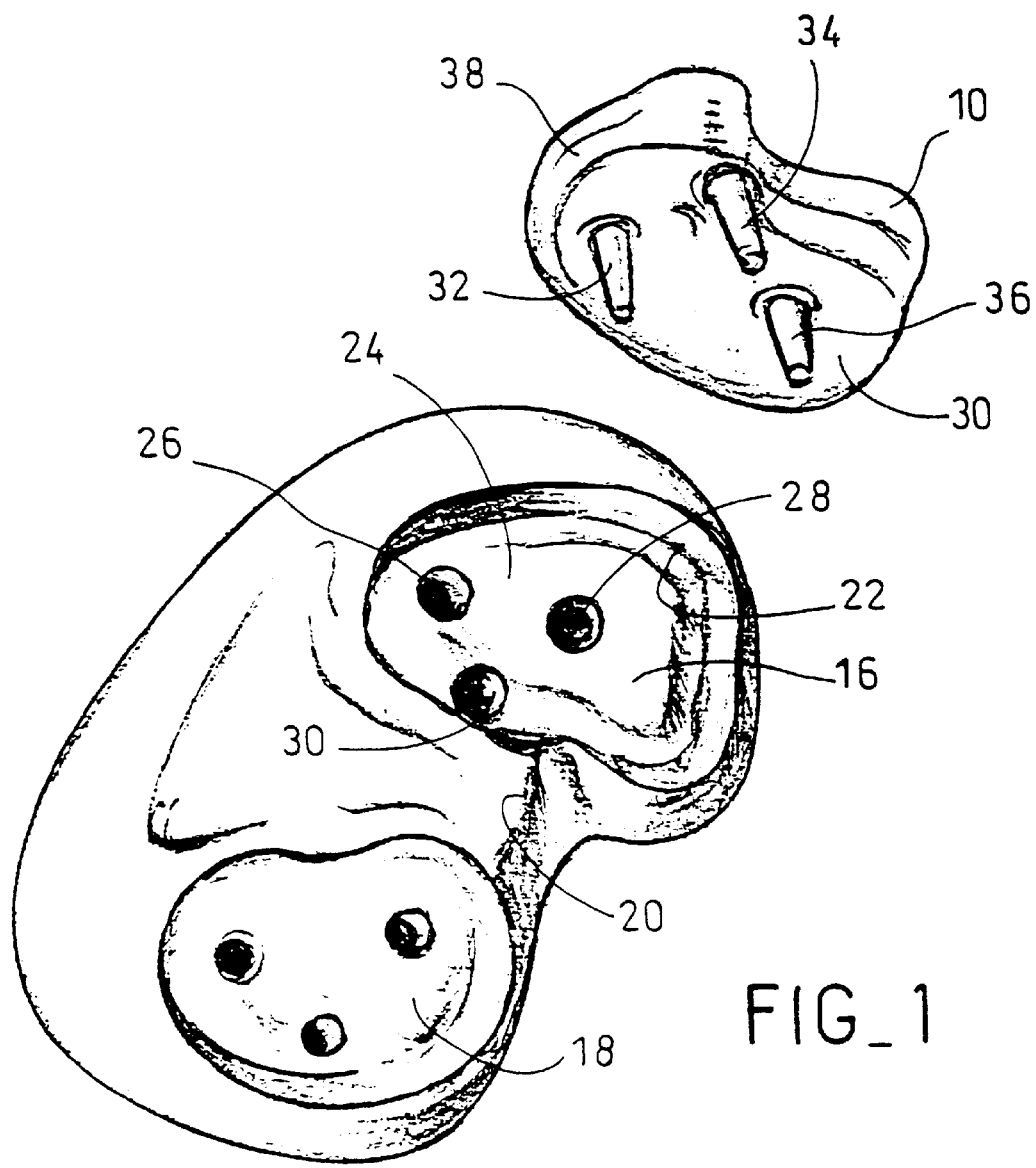
FIG_1a
FIG_1
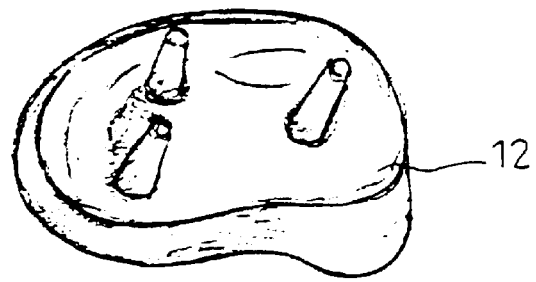
FIG_1b

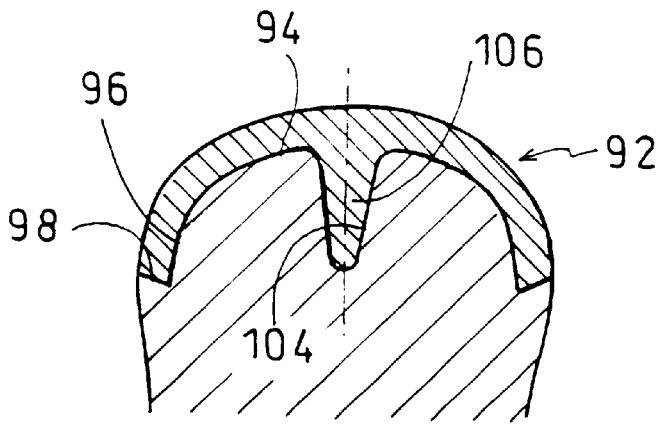
FIG_3b
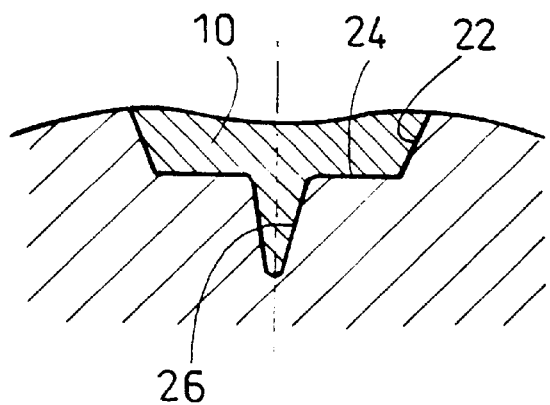
FIG_1c
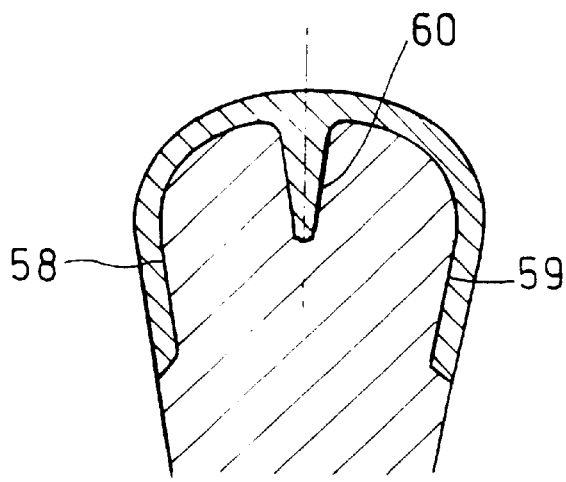
FIG_2b

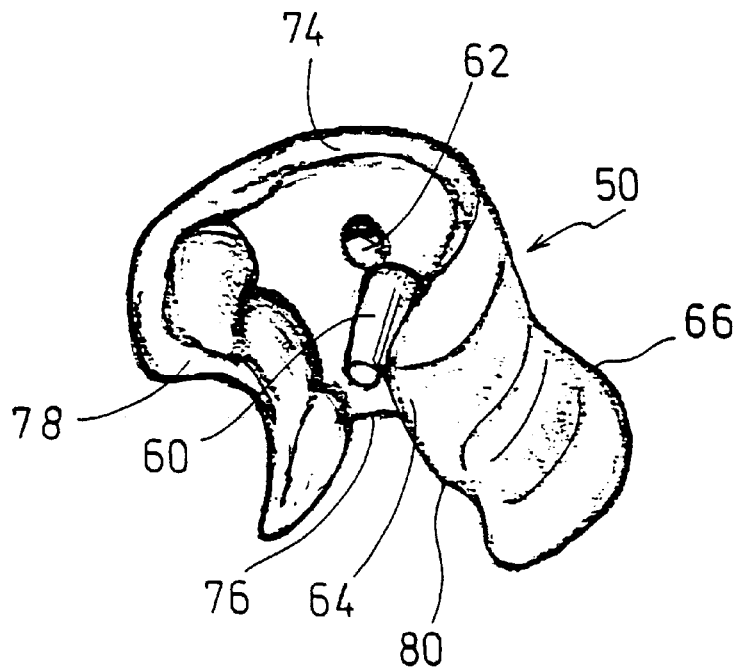
FIG_2a
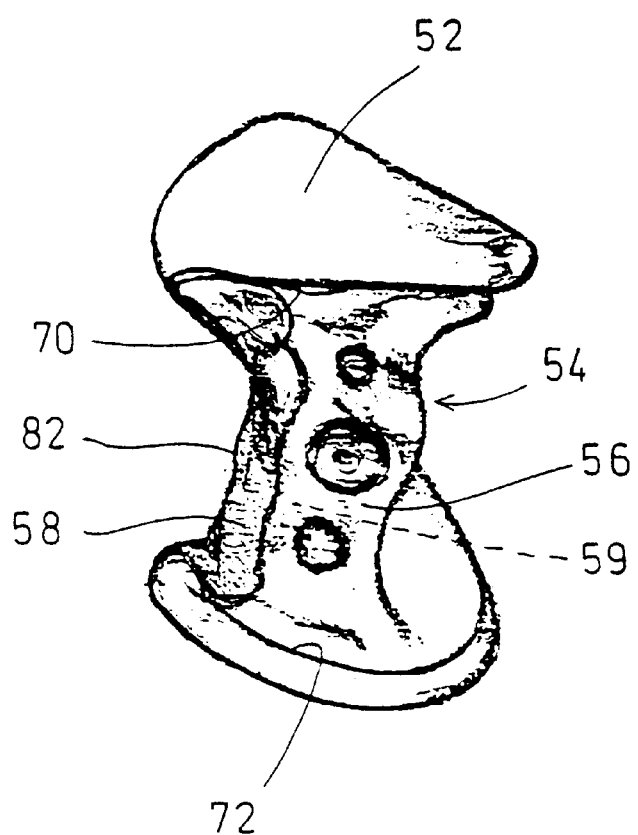
FIG_2

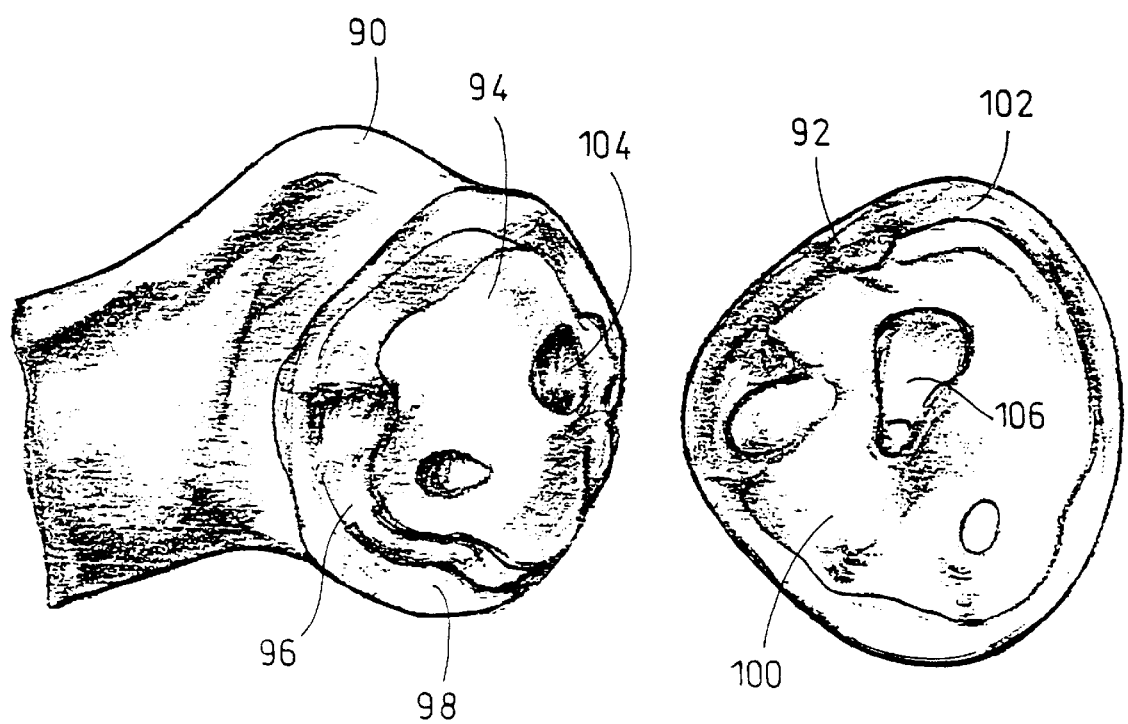
FIG_3  FIG_3a

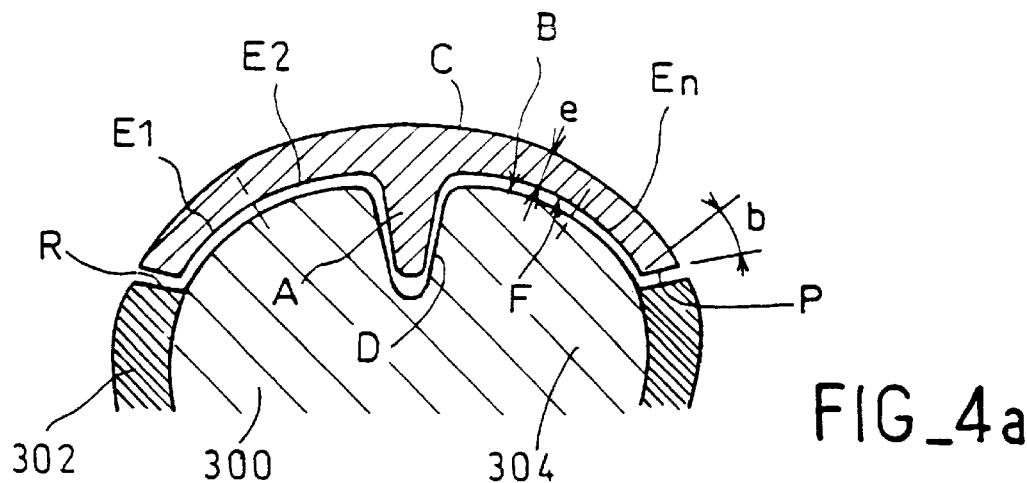
FIG_4a
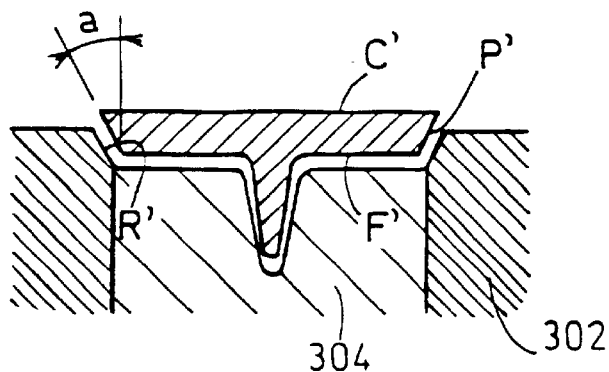
FIG_4b
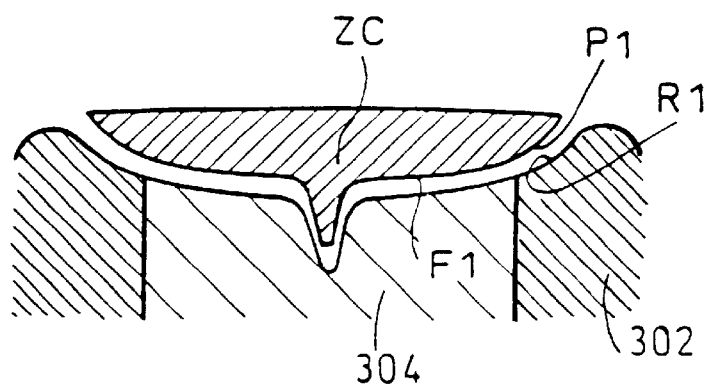
FIG_4c
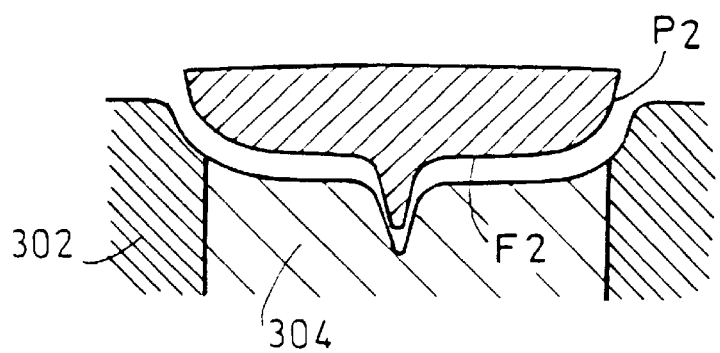
FIG_4d

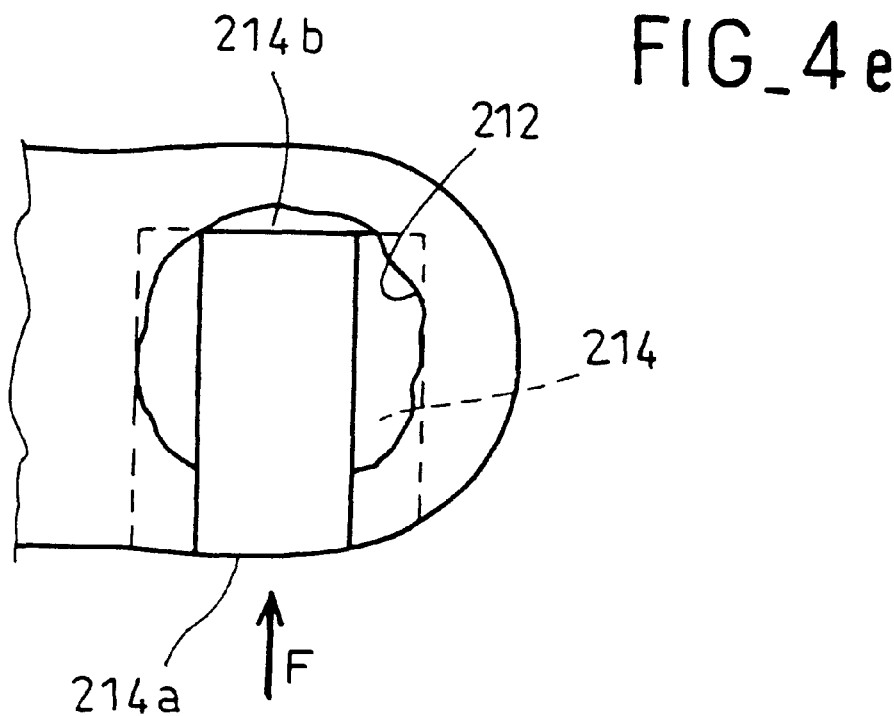
FIG_4e
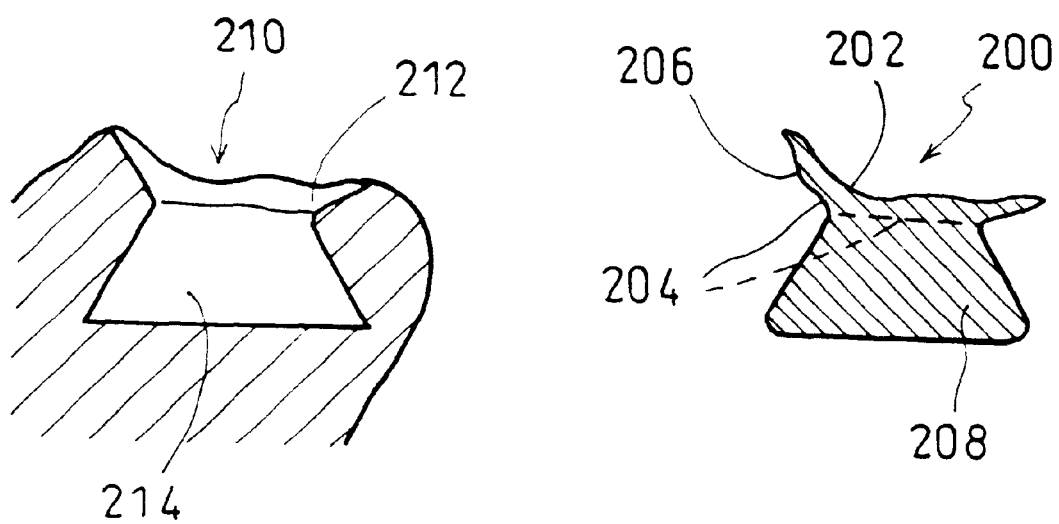
FIG_4f
FIG_4g

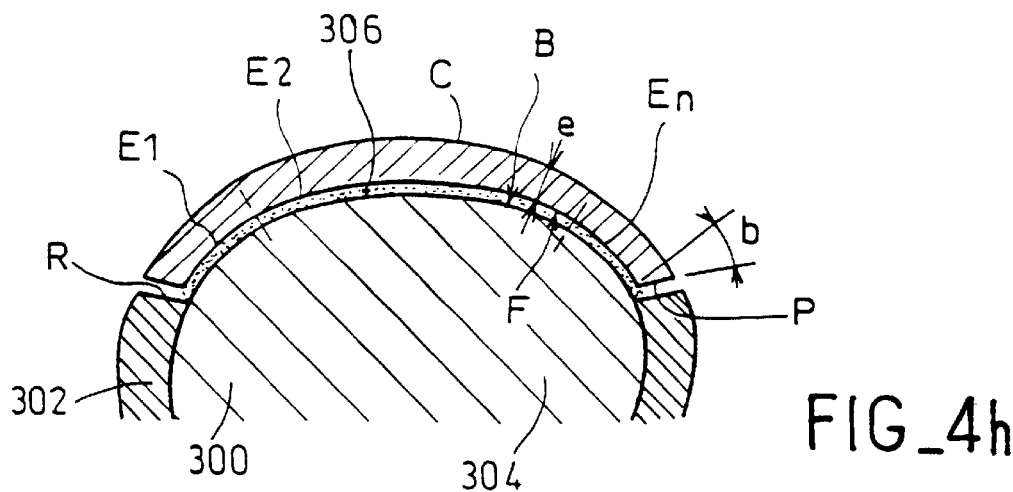
FIG_4h
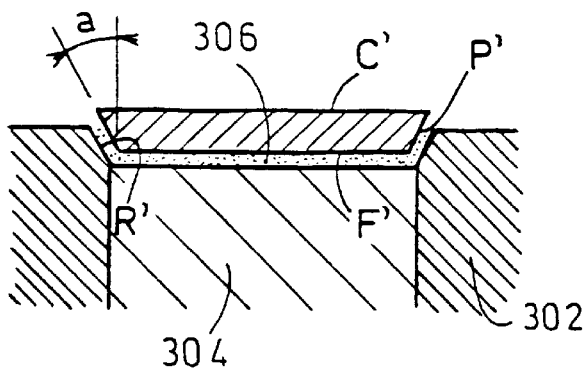
FIG_4i
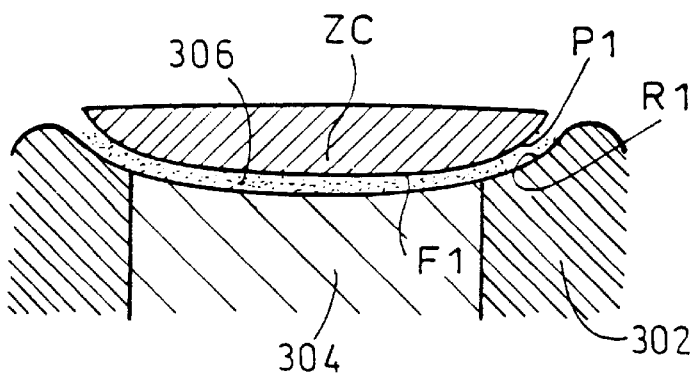
FIG_4j
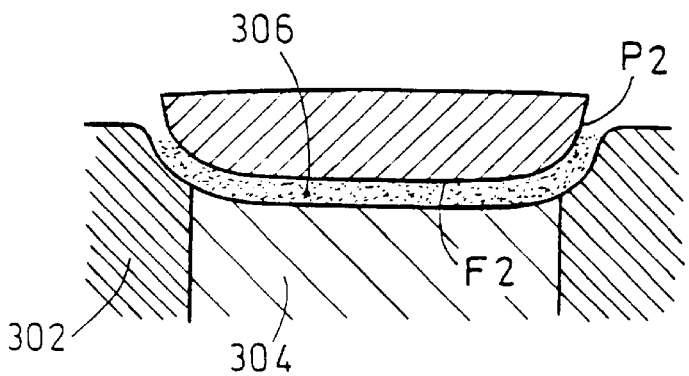
FIG_4k

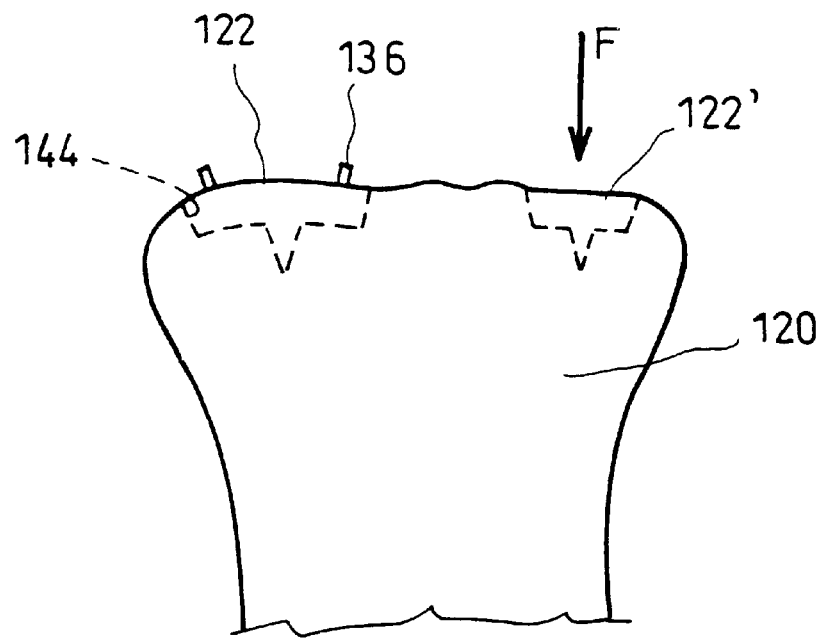
FIG_5
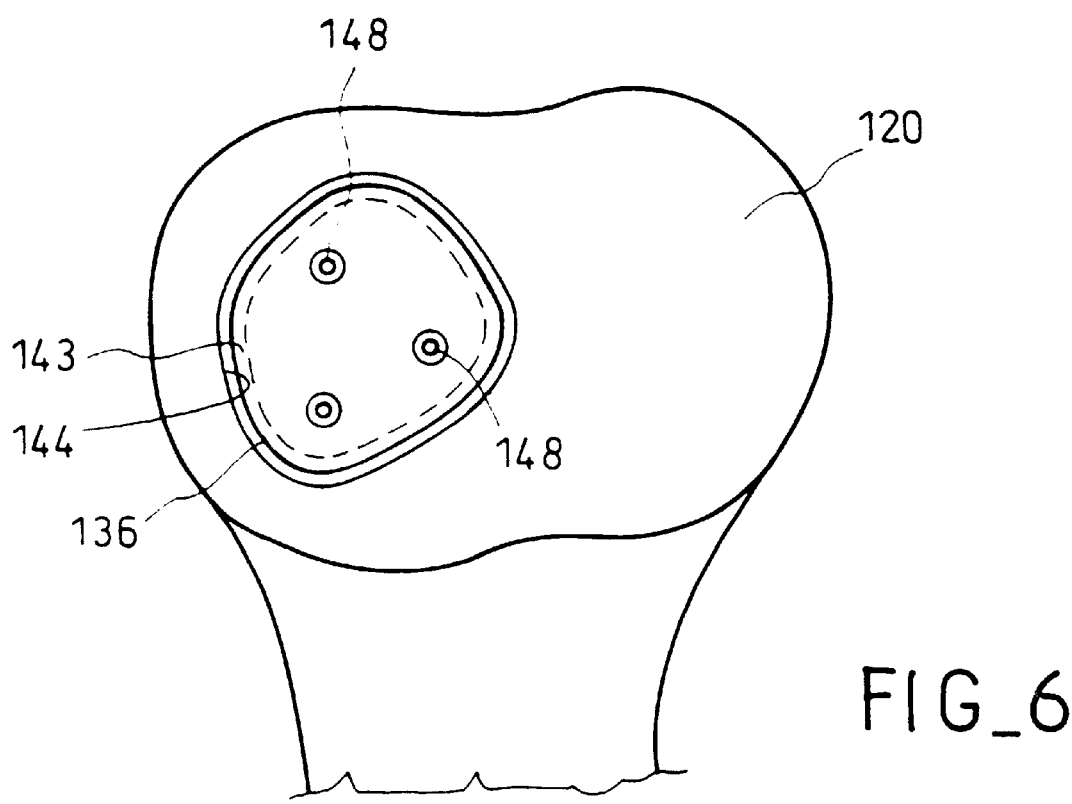
FIG_6

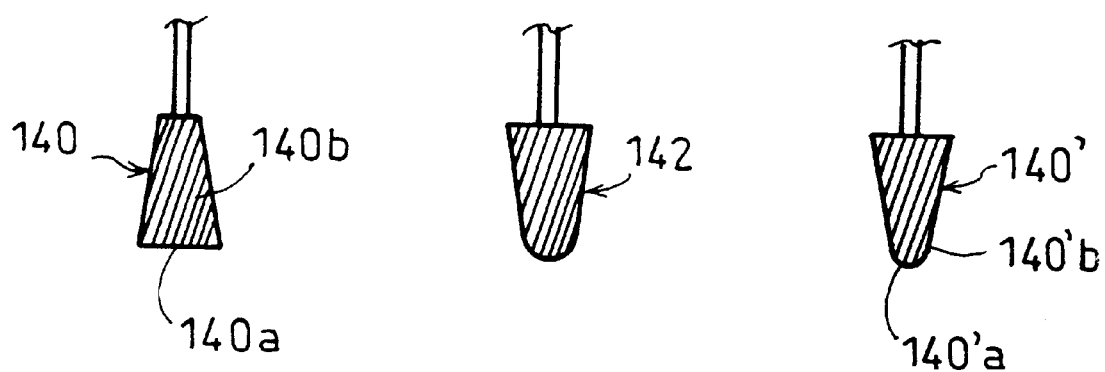
FIG_7a  FIG_7b  FIG_7c
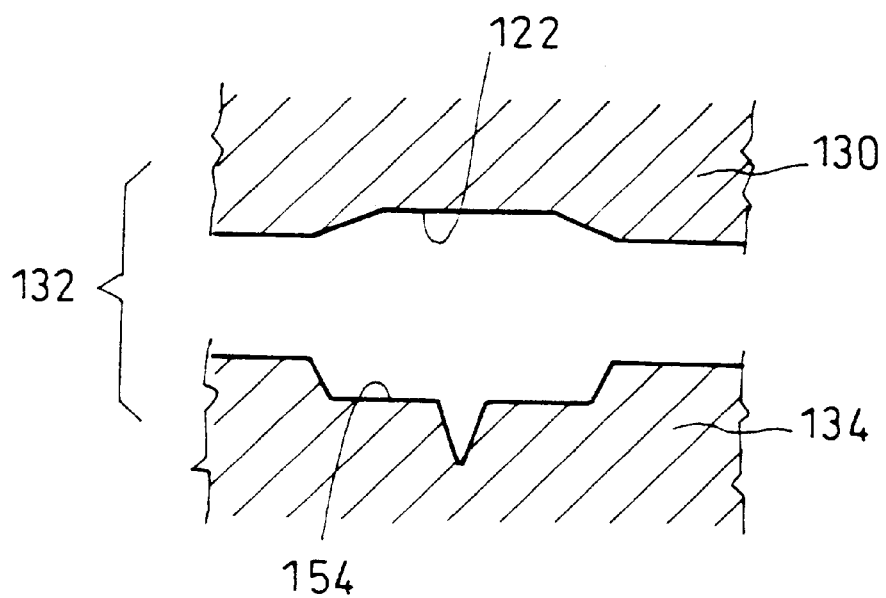
FIG_8

JOINT PROSTHESIS MEMBERS AND METHOD FOR MAKING SAME

This is a continuation of application Ser. No. 09/029,121, filed Jun. 1, 1998 now abandoned, which is a 371 of PCT/FR96/01306 filed Aug. 22, 1996.

The present invention relates to joint prosthesis elements, to a kit for putting joint prosthesis elements into place, and to a method of manufacturing said joint prosthesis elements.

Numerous diseases such as arthrosis or rheumatism, and certain types of accident, lead to various joints deteriorating, and in particular large joints such as the hip, the knee, the shoulder, etc. Such problems or accidents give rise more particularly to destruction of cartilage constituting the surface of the joint. Such deterioration, in particular of cartilage, can lead to the patient who is a victim thereof being seriously handicapped or even badly incapacitated.

In this field, prosthesis elements for use in the knee or hip joint are well known.

With present day techniques, the prosthesis elements used under such circumstances require considerable resection of the joint surfaces, with such resection giving rise either to a plane surface being formed at the end of the bone concerned, or else to a plurality of plane surfaces being formed at angles to one another and constituting an approximation to the real surface of the joint.

Prosthesis elements of that type require a large amount of bone resection in order to be put into place. Such resection in turn requires expensive surgical equipment to be implemented in order to define accurately the plane or planes of the surface of the resection to be performed. In addition, since the resection surface is plane or constituted by a plurality of plane portions, it is necessary to provide anchoring for the prosthesis element that penetrates very deeply into the portion of bone that is associated with the joint surface in order to hold the prosthesis in place. Anchor elements such as screws, pins, studs, etc. require large anchoring holes to be bored in the bone to be treated. Such large boring or drilling in turn requires expensive surgical equipment to be implemented. In addition, the large amount of boring or drilling in the bone can give rise to damaging consequences for that portion of the bone which is subjected to such perforation, in particular concerning its mechanical strength when stresses are applied to the bones constituting the joint when movements are effected, since the length of the anchoring element transfers the force to a zone of the bone that is not intended to withstand such force.

In addition, in the event of a large and substantially plane resection, the thrust of the prosthesis on the resection surface is unsatisfactory since said surface is essentially constituted by spongy bone, and the thrust against the cortical peripheral of the bone is insufficient for taking up the forces.

In addition, known prosthesis elements do not give practitioners a wide enough range of options for providing the degrees of freedom chosen for the joint. Finally, the means used for anchoring such prostheses continue to remain a source of concern with respect to their strength, their stability, and their wear.

An object of the present invention is to provide prosthesis elements for various joints of the human body, which elements require only limited resection of the joint surface while providing very effective anchoring on the portion of bone concerned, and require only the simplest of surgical equipment for putting them into place. Another object of the invention is to provide such a joint prosthesis element which, when all the ligaments of the joint remain intact, makes it possible to restore to the patient all of the degrees of freedom of a healthy joint.

Another object of the invention is to provide a prosthesis element which improves transmission to the bone of the forces applied to the prosthesis.

To achieve this end, the invention provides a joint prosthesis element for fixing to the joint surface of one of the bones of the joint after said joint surface has been subjected to appropriate resection defining a projecting rim over at least a portion of its outline, characterized in that said prosthesis element is defined by a contact surface for co-operating with the prosthesis element of the other bone of the joint, said contact surface being substantially identical to the anatomical joint surface, a fixing surface for fixing to the resection of the joint surface, and a peripheral surface interconnecting said contact and fixing surfaces, said peripheral surface being designed, at least in part, to co-operate with the projecting rim of said resection, which rim corresponds to the cortical portion of the bone, said fixing surface being provided with fixing means, the distance between said contact and fixing surfaces in the central zone thereof and in a fixed direction being substantially constant, said peripheral interconnecting surface including at least some portions that flare relative to said fixing direction from the fixing surface towards the contact surface or from the contact surface towards the fixing surface, whereby said peripheral surface portions bear against the corresponding portions of the rim of said resection.

It will be understood that the prosthesis element is held securely in place on the hinge surface of the bone after resection, in particular because of the shape of the contact surface on the portion of the joint surface that has been subjected to resection and because of the presence of the peripheral surface of the prosthesis element which co-operates with the rim projecting from the resection. As a result, only a relatively small anchoring element need be provided that penetrates a short distance only into the bone, or a layer of adhesive or sealing material, to completely prevent the prosthesis element from moving in any way on the end of the bone.

The invention also provides a kit for putting joint prostheses into place on a joint surface of one of the bones of said joint, the kit being characterized in that it comprises:

a set of similar ones of said prosthesis elements that differ in certain dimensions, each prosthesis element having a contact face for co-operating with a prosthesis of another type fixed on the other bone of said joint, a fixing face for fixing on said joint surface of the bone after it has been subjected to appropriate resection, said fixing face being provided with at least one anchoring element projecting from said face, and a peripheral surface interconnecting said contact and fixing surfaces, each prosthesis element being of substantially constant thickness between said two faces;

a first set of template-forming means for the outline of the resection, each template being associated with one of the prosthesis of the set, each outline template having means for tracing the outline of the resection to be made, said outline corresponding to the periphery of said prosthesis element;

a set of template-forming means for the anchoring holes, each template-forming means being associated with one of the prosthesis elements of the set, each anchoring hole template including means for positioning relative to the outline of the resection and means for tracing the location of the, or each, anchoring hole associated with the anchoring elements;

a first set of instruments, for milling, for making said resection within said outline and for controlling milling parameters;

a second set of instruments, for boring, for making said anchoring holes and controlling the boring parameters; and means for providing assistance in guiding the displacement of said instruments in such a manner that the milling instruments are displaced at least along said outline in such a manner that their axes remain substantially parallel to a fixed direction, said direction being tied to said templates, and in such a manner that the drilling instruments are held on the same drilling axis.

It will be understood that by using physical or optical templates enabling the outline of the resection to be traced and enabling the anchoring hole(s) of the prosthesis element to be positioned, and by using milling to perform the resection, a resection is indeed obtained that makes it possible to use a prosthesis element whose peripheral surface co-operates mechanically with the rim projecting from the resulting resection.

More generally, it will be understood that in its various aspects the invention makes it possible to use prosthesis elements for various joints that are of a shape coinciding with the resection performed by the surgeon when the prosthesis elements are put into place. It will also be understood that because of the substantially constant thickness of such prosthesis elements and because of the peripheral surfaces of such prosthesis elements bearing against the corresponding rims of the resections, prosthesis elements are prevented from moving in a manner that does not require a large amount of anchoring to be provided to hold the prosthesis element on the bone in question, and in particular the anchoring that is provided no longer penetrates a long way into the bone.

The invention also provides a method of manufacturing the above-defined joint prosthesis element, the method being characterized in that it comprises the following steps:

taking a bone having the exact shape of the joint surface of a natural bone for which the prosthesis is to be made;

milling a portion of the extremity of the bone in said joint surface while maintaining a constant milling direction so as to define a milled central zone and a peripheral surface, the depth of milling being substantially constant in said central zone, said peripheral surface defining at least in part a rim that projects from said central zone in the milling direction;

making a mold having a mold cavity that is defined firstly by a first surface defining the contact surface and secondly by a second surface constituted by the fixing surface and said peripheral surface that result from the milling;

putting a molding material into said mold so as to take the shape of the mold cavity;

unmolding the resulting piece, thereby obtaining a prototype for said prosthesis element; and making said prosthesis element from said prosthesis.

The method of manufacturing prosthesis elements makes it possible to give the contact face of the prosthesis element a shape that is identical or quasi-identical to that of the anatomic joint surface prior to resection. This disposition is particularly advantageous when the ligament system of the joint remains intact in the patient being fitted with the prosthesis. In contrast, when the ligament system has been affected and the anatomical degrees of freedom need to be limited accordingly, it is possible to give the contact surface of the prosthesis element a modified shape having greater congruence with the contact surface of the associated prosthesis element so as to limit the relative movements that re possible between the bones forming the joint.

In a first implementation, the fixing means are pegs of generally conical shape penetrating into same-shape anchoring holes.

In a second implementation, the fixing means comprise an anchoring element of dove-tailed shape connected to the central portion of the fixing surface. Under such circumstances, the anchoring hole or orifice is complementary in shape to the anchoring element. To enable the prosthesis element to be put into place, it will be understood that the anchoring hole must open out at one end while it is closed at its other end by bone that has not been subject to resection. Under such circumstances, anchoring advantageously further includes a screw or pin engaged in the free end of the anchoring element in order to prevent the prosthesis element from moving in translation.

In a third implementation, the fixing means comprise a layer of adhesive or sealing material.

Other characteristics and advantages of the invention will appear more clearly on reading on the following description of various embodiments of the invention given as non-limiting examples. The description refers to the accompanying figures, in which:

FIG. 1 is a perspective view of the resection performed on the upper extremity of the tibia;

FIGS. 1a and 1b are perspective views of prosthesis elements to be put into place on the upper extremity of the tibia;

FIG. 1c is a section view through the FIG. 1a prosthesis element when put into place;

FIG. 2 is a perspective view of the resection performed on the lower extremity of the humerus;

FIG. 2a is a perspective view of the prosthesis element for putting into place on the resection of FIG. 2;

FIG. 2b is a section view of the FIG. 2a prosthesis element when put into place;

FIG. 3 is a perspective view of the resection performed on the head of the humerus;

FIG. 3a is a perspective view of the prosthesis element to be put into place on the resection of FIG. 3;

FIG. 3b is a section view of the FIG. 3a prosthesis element put into place;

FIG. 4a is a simplified section view of a first type of prosthesis element;

FIG. 4b is a section view of a second type of prosthesis element;

FIGS. 4c and 4d are section views of third and fourth types of prosthesis element;

FIGS. 4e to 4g show a prosthesis element whose anchoring element is in the form of a dove-tail, FIGS. 4e and 4f showing the resection in plan view and in vertical section, and FIG. 4g showing the prosthesis element in vertical section;

FIGS. 4h to 4k show variant implementations of FIGS. 4a to 4d in which the prosthesis element does not have an anchoring element;

FIG. 5 is an elevation view showing the first step in the method of manufacturing a prosthesis element;

FIG. 6 is a plan view of the joint surface of a bone showing how the resection is defined;

FIGS. 7a, 7b, and 7c show two types of milling cutters usable for manufacturing a prosthesis element; and FIG. 8 is a vertical section view of a mold usable for manufacturing a prosthesis element prototype.

Before describing the shape of the prosthesis elements in detail, the general principle of the present invention is recalled. The prosthesis elements are implanted in resections previously made by the surgeon on the joint surfaces. Because of the bit of instruments (described below) made available to surgeons for performing such resections and because of the way in which prosthesis elements are manufactured (the manufacturing method being described below), it is possible to obtain a close geometrical fit between the shape of the resection formed in the joint surface and the shape of the prosthesis element to be put into place.

This provides a high quality mechanical connection between the prosthesis element and the corresponding bone.

As shown in FIG. 4a, each prosthesis element is limited by a contact surface C, by a fixing surface F, and by a peripheral surface P which interconnects the surfaces C and F. In addition, the fixing surface F is optionally provided with at least one anchoring element A which projects from the fixing face F and forms an integral portion of the prosthesis.

Turning now to the resection performed by the surgeon in the joint surface to enable the prosthesis element to be put into place, said resection comprises a thrust surface B, a peripheral rim projecting from the thrust surface B and referenced R, and optionally at least one anchoring orifice D. This general organization of the prosthesis element and the corresponding resection is to be found regardless of the particular joint surface on which the prosthesis element is put into place.

As shown in FIG. 4a, in the resection zone the bone 300 has a peripheral cortical portion 302 of small thickness and presenting high mechanical strength, and a central portion 304 constituted by spongy bone which has been shown to be of much less mechanical strength. The resection is performed in such a manner that the rim R is entirely constituted by the cortical portion 302 of the bone.

As explained below, by means of the instruments made available to the surgeon for performing the resection and by means of the particular technique used for manufacturing the prosthesis element, it is possible to obtain a substantially perfect geometrical match between the fixing surface F and the thrust surface B of the resection. The prosthesis element is thus embedded in the resection. Similarly, after the prosthesis element has been put into place, it is possible to obtain substantially perfect contact between the peripheral surface P thereof and the peripheral rim R of the resection. Finally, when the anchoring hole D is provided the anchoring element A likewise coincides therewith.

For the prosthesis element of FIG. 4a, the fixing and contact surfaces F and C, in section on planes, are defined by a succession of circular arcs $E_1$, $E_2$, etc. . . . , $E_n$, which run into one another tangentially and which have different radii of curvature. Thus, each portion of the fixing surface has its own "instantaneous center of rotation", thereby further improving the behavior of the prosthesis element. The main part of the prosthesis element is of substantially constant thickness e. Tests have shown that given the material used for making prosthesis elements, it is necessary for the substantially constant thickness e of the prosthesis element to be greater than 6 mm. The tests have shown that with a smaller thickness the prosthesis element is subject to a creep phenomenon is highly prejudicial to the prosthesis keeping good mechanical strength over time. Naturally, the shape of the thrust surface B of the resection corresponds to the shape of the fixing surface F. It will be understood that once the prosthesis element has been put into place it is already mechanically connected to the bone by the presence of its peripheral surface P bearing against the rim R projecting from the resection and because of the special shape of the fixing surface. It will thus be understood that when an anchoring element A is provided, it can be constituted merely by a peg that penetrates into the orifice D of the resection. There is no longer any need to provide a system of pins, screws, studs, or the like. The contact surface C which is to co-operate with the contact surface of the conjugate prosthesis element of the joint is preferably made in such a manner as to comply exactly with the anatomical shape of the joint surface. After the prosthesis element has been put into place in the resection, the initial anatomical joint surface is thus reconstituted exactly. It should be added that the resection is performed in such a manner that where possible it does not interfere with the attachment points of ligaments and muscles, nor with the joint capsule and the surrounding joint surfaces.

To a first approximation, the peripheral surface P is in the form of a truncated non-circular cone. Depending on the nature of the joint surface, the apex of the cone may be disposed on the contact surface side or on the fixing surface side. The angle b between the thickness direction of the prosthesis and the peripheral surface lies in the range 5° to 85°.

For the prosthesis element shown in FIG. 4b, the contact surface C' and the fixing surface F' are substantially plane and mutually parallel in their main portion, the thickness of the element being substantially constant. To a first approximation the peripheral surface P' is a truncated cone whose half-angle at the apex is of the order of 5° to 45°. The peripheral rim R' is complementary in shape to the peripheral surface P'. For prosthesis elements of this type, the resection performed can be considered as a countersink formed by the surgeon in the joint surface.

The apex of the non-circular cone on which the peripheral surface P' lies may be on the same side as the fixing surface F', as shown in FIG. 4b. For certain joint surfaces, particularly on vertebrae, the apex of the cone can be disposed on the same side as the contact surface C'.

In FIGS. 4a and 4b, the peripheral fixing surface P or P' is clearly distinct from the fixing surface F or F'.

With the prosthesis element shown in FIG. 4c, the peripheral surface $P_1$ runs on from the fixing surface $F_1$ substantially without a break. Naturally, in this case, only the central portion ZC of the prosthesis element is of substantially constant thickness. Nevertheless, in this case also the prosthesis element is embedded in the resection and the peripheral surface $P_1$ co-operates with the rim $R_1$ of the resection to participate in fixing the prosthesis.

In the case of FIG. 4d, the peripheral surface $P_2$ differs clearly from the fixing surface $F_2$, however in right section on a plane, said peripheral surface is no longer a rectilinear segment as in FIG. 4a or 4b, but is a portion of a curve. The peripheral surface is thus a skewed surface that can no longer be considered as being a truncated cone.

Whatever the type of prosthesis element under consideration, it will be understood that the peripheral surface P, P' plays a major role in co-operating with the projecting rim of the resection. This contact provides optimum distribution of force transmission between the bone and the prosthesis, thus making it possible, as explained above, to avoid anchoring the prosthesis to the bone by means of large-sized screws, pins, or studs, or the like. It is even possible to avoid having any anchoring element at all and to replace it by means of a layer of a sealing or adhesive material interposed between the fixing face of the prosthesis and the bottom of the resection. Under such circumstances, the fixing face preferably presents a certain degree of roughness to favor adhesion of the material. This is shown in FIGS. 4h to 4k. These figures correspond to FIGS. 4a to 4d except that the anchoring element A is omitted. The layer of sealing or adhesive material is referenced 306 and its thickness has been exaggerated.

It should be added that in the description below, the case described more particularly is that of the means for fixing the prosthesis to the bottom of the resection including at least one anchoring element. Nevertheless, replacing or assisting the anchoring element by means of a layer of sealing or adhesive material does not go beyond the invention.

It is very important to emphasize that angling the peripheral portion P or P' of the prosthesis element that is in contact with the rim R of the resection makes it possible to increase the contact area between these two portions. In addition, this angling makes it possible to alter the direction in which the vertical forces to which the prosthesis is subject are transmitted towards the bone. More precisely, such transmission takes place orthogonally to the contact surface. There is thus a component of these-forces tending to press the prosthesis element against the rim R of the resection. This further improves the effect of embedding the prosthesis in the resection.

In addition, since the rim of the resection is constituted by the cortical portion of the bone, forces transmitted by contact between the periphery of the prosthesis and the rim of the resection are transmitted to the strongest portion of the bone. Depending on the shape of the prosthesis element, it is possible to determine the angling of the periphery of the prosthesis in such a manner that at least 70% of the total force applied to the prosthesis is "taken up" by the cortical portion of the bone. The remainder of the force is taken up by the contact of relatively large area between the fixing face of the prosthesis and the spongy portion of the bone.

The angling of the peripheral zone of the prosthesis is defined as a compromise between the advantage in increasing the contact area with the rim of the resection corresponding to the cortical zone and the fact that it is desirable for the major portion of the prosthesis to have a thickness that is greater than 6 mm so as to avoid creep of its material. Naturally any increase in the contact area causes the prosthesis to be thinner in its peripheral zone.

It will be understood that depending on the section plane taken into consideration, a complete prosthesis element proper may have a configuration similar to that of FIG. 4a or a configuration similar to that of FIG. 4b, 4c, or 4d, or indeed a combination of these various configurations, depending on the section planes under consideration.

In the examples of prosthesis elements described with reference to FIGS. 4a to 4d, the anchoring element is constituted by one or more pegs that are generally conical or frustoconical in shape and that project from the fixing surface, and the anchoring hole is of complementary shape and opens out into the bottom of the resection.

With reference now to FIGS. 4e to 4g, a different embodiment of the anchoring element is described. This anchoring element is generally dove-tailed in shape and the anchoring hole is complementary in shape.

FIG. 4g shows the prosthesis element 200 with its contact surface 202, its fixing surface 204, and its peripheral surface 206. The anchoring element is constituted by a dove-tail shape 208 which is connected to the prosthesis element proper via its fixing surface 204, with the entire element naturally constituting a single piece.

As shown in FIGS. 4e and 4f, the resection 210 formed by the surgeon has a first portion 212 for receiving the prosthesis element proper, and a second portion 214 forming an anchoring hole. The portion 214 is complementary in shape to the dove-tail anchoring element 208. To be able to install the prosthesis, and in particular its anchoring element 208, the portion 214 of the resection has a first end 214a which is open, and a second end 214b which is not open and which is constituted by the remaining portion of the bone. The prosthesis element 200 is put into place in the resection 210 by sliding in the direction of arrow F.

Because of the presence of the fixing surface 204 and of the peripheral surface 206 in combination with the presence of the dove-tailed shape anchoring element 208, the prosthesis element is completely prevented from moving in the resection, except in its insertion direction F.

To remedy this drawback, it is possible to provide a narrow screw or pin whose head projects into the front face of the anchoring element, i.e. its face which remains accessible after the prosthesis has been put into place in the resection. This type of prosthesis is particularly well adapted to vertebrae or even to the top flats of the tibia.

The portion 212 of the resection is milled as described below. The portion 214 is milled using special milling cutters whose axis of rotation is kept parallel to the insertion direction F, the milling machines used having members for controlling the penetration depth to define the desired length of the resection 214 in the direction F.

With reference now to FIGS. 1 to 3, various specific examples of prosthesis elements are described that correspond to various joints.

In FIGS. 1 to 1c, two prosthesis elements 10 and 12 are shown for use on the upper extremity of the tibia. FIG. 1 shows two resections 16 and 18 which are formed while conserving the pre- and retrospinal surfaces, and thus the insertion of the crucial ligaments, of the cartilage, and of the capsule. Each resection includes a projecting thrust rim 22, a thrust surface 24, and three anchoring holes 26, 28, and 30. Each prosthesis element has a fixing surface 30 which is substantially plane and from which three anchoring elements 32, 34, and 36 project. The peripheral surface 38 is generally in the form of a truncated cone, with the differences in thickness in the peripheral zone being due to the fact that the contact surface must connect tangentially to the bone.

As shown better in FIG. 1c, the prosthesis elements 10 and 12 are of the type having fixing and contact surfaces that are substantially plane.

FIGS. 2, 2a, and 2b show the prosthesis element 50 used at the lower extremity of the humerus 52. The thrust surface of the resection 54 has a first portion 56 that is substantially cylindrical in shape and two portions 58 that are substantially plane. The fixing surface of the prosthesis element 50 is naturally of corresponding shape. It has three anchoring elements 60, 62, and 64. The contact surface 66 corresponds to the anatomical joint surface. In planes that are substantially perpendicular to the joint axis, it can be seen that the resection 54 defines two projecting rims 70 and 72 for co-operating with the peripheral surfaces 74 and 76 of the prosthesis. Similarly, the portions 78 and 80 of the peripheral surface of the prosthesis element are designed to co-operate with the projecting rims 82 and 84 that are not visible in the figure. To further improve the behavior of the prosthesis elements, the surfaces 58 and 59 taper slightly towards each other. As can be seen better in FIG. 2b, in the section plane of this figure which is perpendicular to the joint axis, the prosthesis element is of the type shown in FIG. 4b. In contrast, it will be understood that in a section plane containing the joint axis, then the section of the prosthesis element will be of the shape shown in FIG. 4a.

Finally, FIGS. 3, 3a, and 3b show the resection of the head of the humerus and the shape of the corresponding prosthesis element 92. The resection defines a surface portion that can be thought of as a spherical cap 94 connected to a portion 96 that can be thought of as being a more or less cylindrical surface. In addition, this resection has a projecting rim 98 which goes all the way round the resection. It will be understood that in this case the resection leaves an island of bone projecting from the peripheral rim 98. The prosthesis element 92 has a fixing surface 100 corresponding to the surfaces 94 and 96 of the thrust surface of the resection, and an outline and a peripheral surface 102 corresponding to the projecting rim 98. These figures also show the anchoring holes 104 and the anchoring elements.

As already mentioned, one of the essential characteristics of the prosthesis elements lies in the fact that mechanical fixing of prosthesis elements on the joint surface after resection is obtained essentially by the fixing peripheral surface of the prosthesis element and by its fixing surface. This result is obtained by the very great similarity between these portions of the prosthesis element and the peripheral rim and the thrust surface of the resection made by the surgeon when putting the prosthesis element into place. These results can be obtained firstly by the means made available to the surgeon for performing the resection and secondly by the method of manufacturing prosthesis elements.

With reference now to FIGS. 5 to 8, a method of manufacturing a prosthesis element of the invention is described. Initially, as shown in FIG. 5, a bone is used having a joint surface of exactly the shape of a natural bone 120 for which a prosthesis is to be made, the natural bone having a joint surface 122 on which the prosthesis element is to be put into place. In the particular case shown, there are two joint surfaces 122 and 122'. The description below relates only to how the prosthesis element is made that corresponds to the joint surface 122. A reproduction is made of the external anatomical surface shape of the joint surface 122 in order to make a first portion 130 of a mold 132 whose inside face defines a portion of a mold cavity that exactly reproduces the shape of the joint surface.

Thereafter, the bone 120 is milled to have a shape that corresponds exactly to the resection which the surgeon is going to perform on the joint surface of the patient in order to install the prosthesis element. The outline of the resection is defined with the help of a template, which template is given the referenced 136. This template for tracing the outline can be physical or it can be optical. Anatomically speaking, the outline corresponds substantially to the outline of the cartilage. After the resection outline has been drawn, a groove is milled along the outline 36 of the resection using a milling cutter 140 or 142 of the type shown in FIGS. 7a to 7c, and the depth of the groove is predetermined by the shape of the milling cutter 140, 140', or 142. The shape of the cutter is such that the groove 143 defines the projecting rim 144 of the resection. The portion of the joint surface that is defined by the groove 143 that has just been milled is itself removed using other appropriate milling or grinding instruments and using a technique that ensures that substantially the same thickness of bone, or more precisely cartilage is removed at all points. It is important to emphasize that throughout the milling operations for forming the resection, each milling tool is held with its axis parallel to a fixed direction represented by arrow F in FIG. 5. The cutter 140 or 140' has a milling surface not only towards its end 140a (140'a), but also on its side surface 140b (140'b). It will be understood that depending on the position of the drawn outline of the resection relative to the shape of the joint surface, there will be obtained either a groove (FIG. 1 or FIG. 6) or a plane surface (FIG. 2), or a substantially cylindrical surface (FIG. 3). Similarly, depending on circumstances, the resection rim will be milled by the end of the cutter (rim 82 in FIG. 2, rim 98 in FIG. 3) or by its side surface (rim in FIG. 1, rims 70 and 72 in FIG. 2). Also preferably, the axis of the drilling or boring instruments used for making the anchoring holes, when the holes are generally frustoconical in shape, is kept parallel to the drilling direction F. Nevertheless, provision may be made for the axis to be somewhat angled relative to said direction. The anchoring holes are preferably frustoconical as are the corresponding anchoring elements themselves. Thereafter, using a boring template, the positions of the anchoring holes to be made in the resection are marked and the anchoring holes are obtained using a suitable type of boring or milling tool. The anchoring holes are referenced 148 in FIG. 6. Thereafter, any appropriate means are used to take the shape of the resection made in this way, i.e. its peripheral surface 150, its bearing surface 152, and its anchoring holes 148. On the basis of the taken shape of the resection, a second mold element 134 is made whose inside face defining a portion of the mold cavity and referenced 154 has exactly the same shape as the resection. Naturally, the same applies when the anchoring element is dove-tailed in shape. A suitable molding material is injected into the mold 132, e.g. a resin or a wax or some other material, once the mold has been closed. On unmolding, a prototype is obtained for the prosthesis element which has exactly the desired shape concerning its contact face, its fixing face, and its peripheral surface.

From this prototype, is it possible to manufacture prosthesis elements proper by copying its shape using appropriate biocompatible materials such as titanium, polyethylene, or a combination thereof.

The invention also relates to a kit made available to a surgeon for putting prosthesis elements into place.

For each prosthesis element corresponding to a joint surface, the surgeon is given several "sizes" of prosthesis element which differ from one another solely by having different dimensions, all of the prosthesis elements having the same shape. Before the operation, the surgeon uses any appropriate means to determine which size is appropriate.

For each size of prosthesis elements, the surgeon has a template for tracing the outline of the resection that is to be made and a template for drilling the anchoring holes. These templates may either be physical or optical. If they are optical, the template consists in means for projecting the image of the outline or of the anchoring holes onto the joint surface.

Finally, the surgeon has milling, grinding, and/or boring instruments for performing the resection and the anchoring holes, depending on their shapes. Example milling cutters are shown in FIGS. 7a, 7b, and 7c. Each cutter or each boring instrument preferably has a depth reference so that the surgeon performs the resection to the desired substantially constant depth.

As already mentioned, throughout the entire operation of milling the outline of the resection, the axis of rotation of the cutter must remain parallel to a given direction which is defined for each prosthesis element.

The surgeon may have physical or optical guide means available for assisting in holding the cutter manually in the desired direction.

What is claimed is:
1. A joint prosthesis for fixing the joint surface of one of the bones of the joint after said joint surface has been subjected to appropriate resection defining a projecting rim over at least a portion of its outline, characterized in that said joint defined by a contact surface for co-operating with the prosthesis element of the other bone of the joint, said contact surface being substantially identical to the anatomical joint surface, a fixing surface for fixing to the resection of the joint surface, and a peripheral surface interconnecting said contact and fixing surfaces, said peripheral surface being formed, at least in part, to co-operate with the projecting rim of said resection, which rim corresponds to the cortical portion of the bone, said fixing surface being provided with fixing means, the distance between said contact and fixing surfaces in the central zone thereof and in a fixed direction being substantially constant, said peripheral surface including at least some portions that flare relative to said fixing direction from the fixing surface towards the contact surface or from the contact surface towards the fixing surface, whereby said peripheral surface portions bear against the corresponding portions of the rim of said resection;

further characterized in that said angle a is determined so that at least 70% of the forces received by the prosthesis element are applied to the cortical portion of that bone.

2. A prosthesis element according to claim 1, characterized in that the fixing means comprise a layer of sealing or adhesive material, and in that the fixing surface has sufficient roughness to enhance the adhesion of said material.

3. A prosthesis element according to claim 1, characterized in that the fixing means comprise at least one anchoring element projecting from the fixing surface and forming an integral part of said prosthesis element.

4. A prosthesis element according to claim 3, characterized in that the anchoring element comprises at least one peg of substantially frustoconical shape made out of the same material as the remainder of the prosthesis element.

5. A prosthesis element according to claim 3, characterized in that said anchoring element is substantially dovetailed in shape projecting from said fixing face.

6. A prosthesis element according to claim 1, characterized in that said fixing surface is substantially plane, in that said contact surface is also substantially plane and substantially parallel to the fixing surface, in that said anchoring elements are substantially orthogonal to said fixing surface, and in that said peripheral surface is at an angle a lying in the range 5° to 45° with a direction normal to said contact surfaces, flaring towards said contact surface occupying said peripheral surface occupying substantially all of the outline of said contact and fixing surfaces.

7. A prosthesis element according to claim 1, characterized in that the contact and fixing surfaces are defined in section on a first family of mutually parallel planes by a plurality of circular arcs that are connected together tangentially, said circular arcs having distinct centers.

8. A prosthesis element according to claim 1, characterized in that the contact and fixing surfaces are defined in section on a first family of mutually parallel planes by a plurality of circular arcs that are connected together tangentially, and in that the section on said planes of the interconnecting peripheral surface forms a contact angle b with the tangent at the end of the section of the contact surface where b lies in the range of 50° to 85°, flaring towards said-fixing surface.

9. A prosthesis element according to claim 1, characterized in that said peripheral surface is substantially in the form of a truncated cone of non-circular right section.

10. A kit for putting a joint prosthesis element according to claim 1 into place on a joint surface of one of the bones of said joint, the kit being characterized in that it comprises:

a set of similar ones of said prosthesis elements that differ in certain dimensions, each prosthesis element having a contact face for co-operating with a prosthesis of another type fixed on the other bone of said joint, a fixing face for fixing on said joint surface of the bone after it has been subjected to appropriate resection, said fixing face being provided with at least one anchoring element projecting from said face, and a peripheral surface interconnecting said contact and fixing-surfaces, each prosthesis element being of substantially constant thickness between said two faces;

a first set of template-forming means for the outline of the resection, each template being associated with one of the prosthesis of the set, each outline template having means for tracing the outline of the resection to be made, said outline corresponding to the periphery of said prosthesis element;

a set of template-forming means for the anchoring holes, each template-forming means being associated with one of the prosthesis elements of the set, each anchoring hole template including means for positioning relative to the outline of the resection and means for tracing the location of the, or each, anchoring hole associated with the anchoring elements;

a first set of instruments, for milling, for making said resection within said outline and for controlling milling parameters;

a second set of instruments, for boring, for making said anchoring holes and controlling the boring parameters; and means for providing assistance in guiding the displacement of said instruments in such a manner that the milling instruments are displaced at least along said outline in such a manner that their axes remain substantially parallel to a fixed direction, said direction being tied to said templates, and in such a manner that the drilling instruments are held on the same drilling axis.

11. A kit according to claim 10, characterized in that it further includes a set of test prosthesis elements, each test prosthesis element corresponding to a prosthesis element and having exactly the same shape, each test prosthesis element including putting into place means.

12. A joint prosthesis for fixing the joint surface of one of the bones of the joint after said joint surface has been subjected to appropriate resection defining a projecting rim over at least a portion of its outline, characterized in that said joint defined by a contact surface for co-operating with the prosthesis element of the other bone of the joint, said contact surface being substantially identical to the anatomical joint surface, a fixing surface for fixing to the resection of the joint surface, and a peripheral surface interconnecting said contact and fixing surfaces, said peripheral surface being formed, at least in part, to co-operate with the projecting rim of said resection, which rim corresponds to the cortical portion of the bone, said fixing surface being provided with fixing means, the distance between said contact and fixing surfaces in the central zone thereof and in a fixed direction being substantially constant, said peripheral surface including at least some portions that flare relative to said fixing direction from the fixing surface towards the contact surface or from the contact surface towards the fixing surface, whereby said peripheral surface portions bear against the corresponding portions of the rim of said resection;

further characterized in that said peripheral surface is substantially in the form of a truncated cone of non-circular right section.

13. A prosthesis element according to claim 12, characterized in that the fixing means comprise a layer of sealing or adhesive material, and in that the fixing surface has sufficient roughness to enhance the adhesion of said material.

14. A prosthesis element according to claim 12, characterized in that the fixing means comprise at least one anchoring element projecting from the fixing surface and forming an integral part of said prosthesis element.

15. A prosthesis element according to claim 14 characterized in that the anchoring element (A) comprises at least one peg of substantially frustoconical shape made out of the same material as the remainder of the prosthesis element.

16. A prosthesis element according to claim 14 characterized in that said anchoring element is substantially dovetailed in shape projecting from said fixing face.

17. A prosthesis element according to claim 12, characterized in that said fixing surface is substantially plane, in that said contact surface is also substantially plane and substantially parallel to the fixing surface, in that said anchoring elements are substantially orthogonal to said fixing surface, and in that said peripheral surface is at an angle a lying in the range 5° to 45° with a direction normal to said contact surfaces, flaring towards said contact surface occupying said peripheral surface and occupying substantially all of the outline of said contact and fixing surfaces.

18. A prosthesis element according to claim 17, characterized in that said angle a is determined so that at least 70% of the forces received by the prosthesis element are applied to the cortical portion of the bone.

19. A prosthesis element according to claim 12, characterized in that said fixing surface is substantially plane, in that said contact surface is also substantially plane and substantially parallel to the fixing surface, in that said anchoring elements are substantially orthogonal to said fixing surface, and in that said peripheral surface is at an angle a lying in the range 5° to 45° with the direction normal to said contact surfaces, flaring towards said fixing surface occupying said peripheral surface occupying substantially all of the outline of said contact and fixing surfaces.

20. A prosthesis element according to claim 12, characterized in that the contact and fixing surfaces are defined in section on a first family of mutually parallel planes by a plurality of circular arcs that are connected together tangentially, said circular arcs having distinct centers.

21. A prosthesis element according to claim 12, characterized in that the contact and fixing surfaces are defined in section on a first family of mutually parallel planes by a plurality of circular arcs that are connected together tangentially, and in that the section on said planes of the interconnecting peripheral surface forms a contact angle b with the tangent at the end of the section of the contact surface where b lies in the range of 50° to 85°, flaring towards said-fixing surface.

22. A kit for putting a joint prosthesis element according to claim 12 into place on a joint surface of one of the bones of said joint, the kit being characterized in that it comprises:

a set of similar ones of said prosthesis elements that differ in certain dimensions, each prosthesis element having a contact face for co-operating with a prosthesis of another type fixed on the other bone of said joint, a fixing face for fixing on said joint surface of the bone after it has been subjected to appropriate resection, said fixing face being provided with at least one anchoring element projecting from said face, and a peripheral surface interconnecting said contact and fixing-surfaces, each prosthesis element being of substantially constant thickness between said two faces;

a first set of template-forming means for the outline of the resection, each template being associated with one of the prosthesis of the set, each outline template having means for tracing the outline of the resection to be made, said outline corresponding to the periphery of said prosthesis element;

a set of template-forming means for the anchoring holes, each template-forming means being associated with one of the prosthesis elements of the set, each anchoring hole template including means for positioning relative to the outline of the resection and means for tracing the location of the, or each, anchoring hole associated with the anchoring elements;

a first set of instruments, for milling, for making said resection within said outline and for controlling milling parameters;

a second set of instruments, for boring, for making said anchoring holes and controlling the boring parameters; and means for providing assistance in guiding the displacement of said instruments in such a manner that the milling instruments are displaced at least along said outline in such a manner that their axes remain substantially parallel to a fixed direction, said direction being tied to said templates, and in such a manner that the drilling instruments are held on the same drilling axis.

23. A kit according to claim 22, characterized in that it further includes a set of test prosthesis elements, each test prosthesis element corresponding to a prosthesis element and having exactly the same shape, each test prosthesis element including putting into place means.

24. A joint prosthesis for fixing the joint surface of one of the bones of the joint after said joint surface has been subjected to appropriate resection defining a projecting rim over at least a portion of its outline, characterized in that said joint defined by a contact surface for co-operating with the prosthesis element of the other bone of the joint, said contact surface being substantially identical to the anatomical joint surface, a fixing surface for fixing to the resection of the joint surface, and a peripheral surface interconnecting said contact and fixing surfaces, said peripheral surface being formed, at least in part, to co-operate with the projecting rim of said resection, which rim corresponds to the cortical portion of the bone, said fixing surface being provided with fixing means, the distance between said contact and fixing surfaces in the central zone thereof and in a fixed direction being substantially constant, said peripheral surface including at least some portions that flare relative to said fixing direction from the fixing surface towards the contact surface or from the contact surface towards the fixing surface, whereby said peripheral surface portions bear against the corresponding portions of the rim of said resection;

further characterized in that said distance between the fixing surface and the contact surface and the contact surface is at least 6 mm.

25. A prosthesis element according to claim 24, characterized in that the fixing means comprise a layer of sealing or adhesive material, and in that the fixing surface has sufficient roughness to enhance the adhesion of said material.

26. A prosthesis element according to claim 24, characterized in that the fixing means comprise at least one anchoring element projecting from the fixing surface and forming an integral part of said prosthesis element.

27. A prosthesis element according to claim 26, characterized in that the anchoring element comprises at least one peg of substantially frustoconical shape made out of the same material as the remainder of the prosthesis element.

28. A prosthesis element according to claim 26, characterized in that said anchoring element is substantially dovetailed in shape projecting from said fixing face.

29. A prosthesis element according to claim 24, characterized in that said fixing surface is substantially plane, in that said contact surface is also substantially plane and substantially parallel to the fixing surface, in that said anchoring elements are substantially orthogonal to said fixing surface, and in that said peripheral surface is at an angle a lying in the range 5° to 45° with a direction normal to said contact surfaces, flaring towards said contact surface occupying said peripheral surface occupying substantially all of the outline of said contact and fixing surfaces.

30. A prosthesis element according to claim 29, characterized in that said angle a is determined so that at least 70% of the forces received by the prosthesis element are applied to the cortical portion of the bone.

31. A prosthesis element according to claim 24, characterized in that said fixing surface is substantially plane, in that said contact surface is also substantially plane and substantially parallel to the fixing surface, in that said anchoring elements are substantially orthogonal to said fixing surface, and in that said peripheral surface is at an angle a lying in the range 5° to 45° with the direction normal to said contact surfaces, flaring towards said fixing surface occupying said peripheral surface occupying substantially all of the outline of said contact and fixing surfaces.

32. A prosthesis element according to claim 24, characterized in that the contact and fixing surfaces are defined in section on a first family of mutually parallel planes by a plurality of circular arcs that are connected together tangentially, said circular arcs having distinct centers.

33. A prosthesis element according to claim 24, characterized in that the contact and fixing surfaces are defined in section on a first family of mutually parallel planes by a plurality of circular arcs that are connected together tangentially, and in that the section on said planes forms a contact angle b with the tangent at the end of the section of the contact surface where b lies in the range of 50° to 85°, flaring towards said-fixing surface.

34. A prosthesis element according to claim 24, characterized in that said peripheral surface is substantially in the form of a truncated cone of non-circular right section.

35. A kit for putting a joint prosthesis element according to claim 12 into place on a joint surface of one of the bones of said joint, the kit being characterized in that it comprises:
 a set of similar ones of said prosthesis elements that differ in certain dimensions, each prosthesis element having a contact face for co-operating with a prosthesis of another type fixed on the other bone of said joint, a fixing face for fixing on said joint surface of the bone after it has been subjected to appropriate resection, said fixing face being provided with at least one anchoring element projecting from said face, and a peripheral surface interconnecting said contact and fixing-surfaces, each prosthesis element being of substantially constant thickness between said two faces;
 a first set of template-forming means for the outline of the resection, each template being associated with one of the prosthesis of the set, each outline template having means for tracing the outline of the resection to be made, said outline corresponding to the periphery of said prosthesis element;
 a set of template-forming means for the anchoring holes, each template-forming means being associated with one of the prosthesis elements of the set, each anchoring hole template including means for positioning relative to the outline of the resection and means for tracing the location of the, or each, anchoring hole associated with the anchoring elements;
 a first set of instruments, for milling, for making said resection within said outline and for controlling milling parameters;
 a second set of instruments, for boring, for making said anchoring holes and controlling the boring parameters; and
 means for providing assistance in guiding the displacement of said instruments in such a manner that the milling instruments are displaced at least along said outline in such a manner that their axes remain substantially parallel to a fixed direction, said direction being tied to said templates, and in such a manner that the drilling instruments are held on the same drilling axis.

36. A kit according to claim 35, characterized in that it further includes a set of test prosthesis elements, each test prosthesis element corresponding to a prosthesis element and having exactly the same shape, each test prosthesis element including putting into place means.

37. A method of manufacturing a joint prosthesis-element, the method being characterized in that it comprises the following steps:
 taking a bone having the exact shape of the joint surface of a natural bone for which the prosthesis is to be made;
 milling a portion of the extremity of the bone in said joint surface while maintaining a constant milling direction so as to define a milled central zone and a peripheral surface, the depth of milling being substantially constant in said central zone, said peripheral surface defining at least in part a rim that projects from said central zone in the milling direction;
 making a mold having a mold cavity that is defined firstly by a first surface defining the contact surface and secondly by a second surface constituted by the fixing surface and said peripheral surface that result from the milling;
 putting a molding material into said mold so as to take the shape of the mold cavity;
 unmolding the resulting piece, thereby obtaining a prototype for said prosthesis element; and
 making said prosthesis element from said prosthesis.

* * * * *